US00PP35169P3

(12) United States Plant Patent
Ruter

(10) Patent No.: US PP35,169 P3
(45) Date of Patent: May 16, 2023

(54) ***ILEX* PLANT NAMED 'RUTHOL5'**

(50) Latin Name: ***hybrid Ilex* cultivar**
Varietal Denomination: RutHol5

(71) Applicant: University of Georgia Research Foundation, Inc., Athens, GA (US)

(72) Inventor: John M. Ruter, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/882,849

(22) Filed: Aug. 8, 2022

(65) Prior Publication Data

US 2023/0045785 P1 Feb. 9, 2023

Related U.S. Application Data

(60) Provisional application No. 63/230,218, filed on Aug. 6, 2021.

(51) Int. Cl.
*A01H 5/00* (2018.01)
*A01H 6/00* (2018.01)

(52) U.S. Cl.
USPC ..... Plt./247
CPC ..... *A01H 6/00* (2018.05)

(58) Field of Classification Search
USPC ..... Plt./226, 247
See application file for complete search history.

*Primary Examiner* — Karen M Redden
(74) *Attorney, Agent, or Firm* — Thomas Horstemeyer, LLP

(57) ABSTRACT

A new and distinct cultivar of *Ilex* plant named 'RutHol5', characterized by its upright, narrow form with widest spread in the middle of the canopy that narrows towards the top; a height-to-width ratio of about 3.2; reddish colored new growth, and resistance to spider mites, *Tetranychus urticae*.

2 Drawing Sheets

Figure 1:
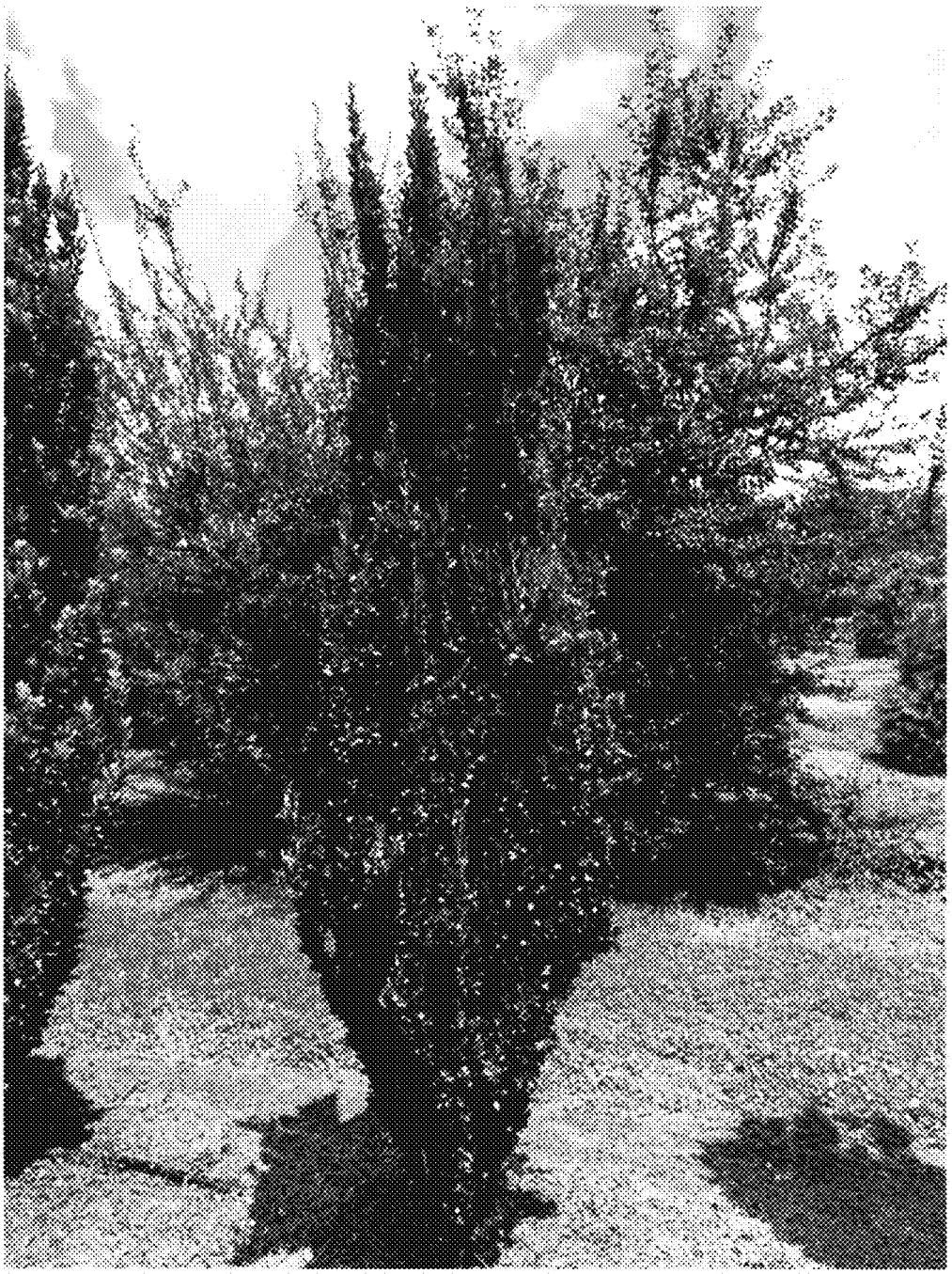

Botanical designation: hybrid *Ilex* cultivar.
Cultivar denomination 'RutHol5'.

BACKGROUND OF THE INVENTION

The present invention relates to a new and distinct hybrid cultivar of *Ilex* (holly), and hereinafter referred to by the cultivar name 'RutHol5'.

The new *Ilex* cultivar is the product of a planned breeding program conducted by the inventor in Watkinsville, Ga. The objective of the *Ilex* breeding program is to create new plant cultivars with novel forms of growth, good cold hardiness, and resistance to damage from spider mites, insects and diseases.

The new *Ilex* cultivar 'RutHol5' is a product of an open pollinated cross between F1 seedlings (unpatented and no longer available) from an original cross of *Ilex crenata* (unpatented) and *Ilex maximowicziana* (unpatented). 'RutHol5' has been evaluated for container production and evaluated through trials at a horticultural farm in Watkinsville, Ga. since about 2016.

Asexual reproduction of the new *Ilex* cultivar has been continued by vegetative terminal cuttings in a controlled environment in Dearing, Ga. and Watkinsville, Ga. since about 2014. Observations of the resulting progeny have shown that the unique features of the new *Ilex* cultivars are stable and reproduced true to type in successive generations.

SUMMARY OF THE INVENTION

The new *Ilex* cultivar 'RutHol5' has not been observed under all possible environmental conditions. The phenotypes may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new *Ilex* cultivar named 'RutHol5'. In combination, this combination of traits set 'RutHol5' apart from all other existing varieties of *Ilex*, including the parents, known to the inventors.

1. Upright growth that is widest in the middle of the canopy and narrowing toward the top;
2. Narrow, densely conical growth habit with a height: width ratio of about 3.2;
3. New growth that is reddish colored in contrast to black-green mature leaves; and
4. Resistance to spider mites *Tetranychus urticae*.

Plants of the 'RutHol5' differ from the most similar *Ilex* cultivars based on at least some of the above characteristics. The two F1 seedling parents of 'RutHol5' no longer exist, so detailed comparison is not possible; however, neither parent had the reddish colored new growth of 'RutHol5'. 'RutHol5' differs from grandparent cultivar *Ilex maximowicziana* in at least that *Ilex maximowicziana* did not feature reddish new growth, had a more acute leaf aspect (45° vs 55-65° for 'RutHol5'), and had a smaller leaf length-to-width ratio (2.0 vs. 2.3 for 'RutHol5'). 'RutHol5' can also be compared to commercial cultivar *Ilex crenata* 'PIIIC-I' (U.S. Plant Pat. No. 29,578), which has cupped rather than elliptical leaves, does not have the reddish colored new growth of 'RutHol5', and has less compact mature growth. 'RutHol5' is also faster growing and has more resistance to spider mites (*Tetranychus urticae*) as compared to 'PIIIC-I'.

BRIEF DESCRIPTION OF THE PHOTOGRAPHS

The accompanying colored photographic illustrations show the overall appearance and distinct characteristics of the new cultivar of *Ilex* 'RutHol5' showing the colors as true as possible. Colors in the photographs may differ slightly from the color values cited in the detailed botanical description. The photographs were taken of plants grown outdoors in Watkinsville, Ga. in May 2021 and are described in the captions below.

The photograph labeled FIG. 1 depicts a full view of a typical 6-year-old 'RutHol5' plant showing the narrow, densely conical growth habit, and shape with widest spread near the middle of the canopy with narrowing toward the top.

Figure 2:
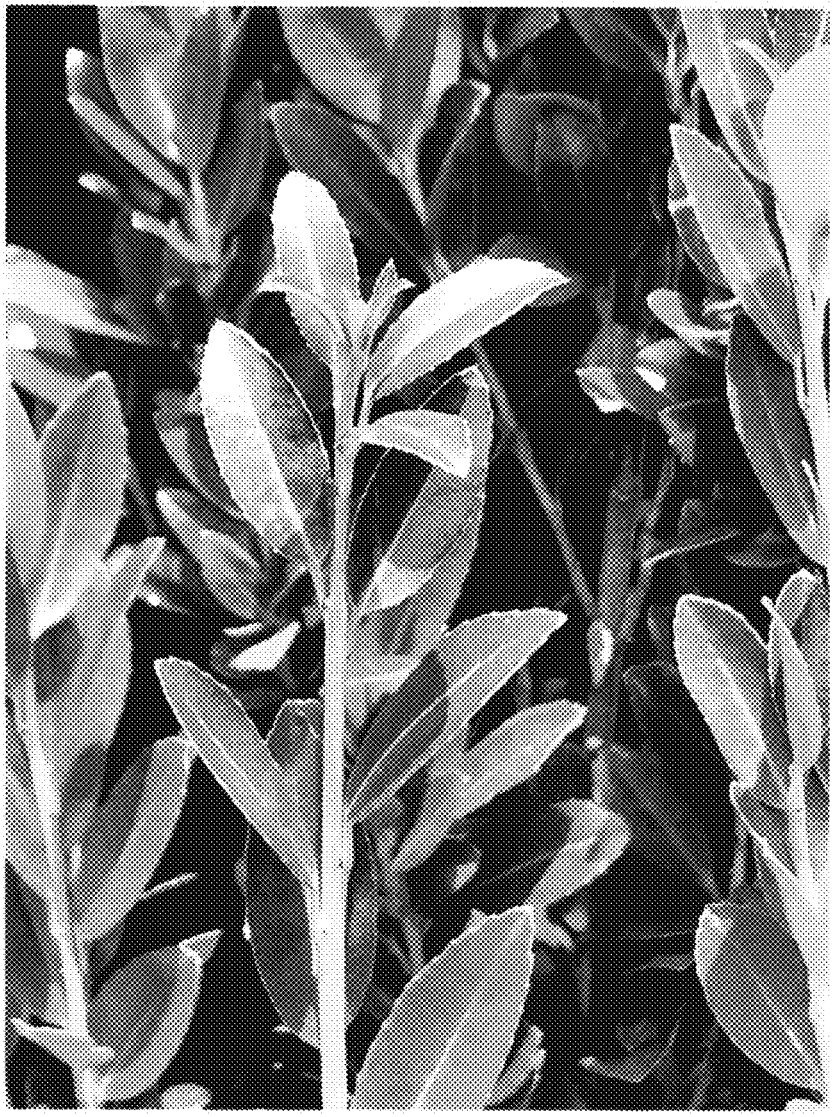

The photograph labeled FIG. 2 depicts a close-up view of some branches of a typical 6-year-old 'RutHol5' plant showing the reddish colored new growth.

DETAILED BOTANICAL DESCRIPTION

The following traits have been consistently observed in the original plants of the new 'RutHol5' and in asexually propagated progeny grown in Watkinsville, Ga., and, to the best knowledge of the inventors, their combination forms the unique characteristics of the new variety *Ilex* 'RutHol5'.

Throughout this specification, color names beginning with a small letter signify that the name of that color, as used in common speech, is aptly descriptive. Color names beginning with a capital letter designate values based upon The R.H.S. Colour Chart, $6^{th}$ edition published by The Royal Horticultural Society, London, England in 2015, except where general terms of ordinary dictionary significance are used.

The aforementioned photographs and following observations, measurements, and values describe plants of the *Ilex* cultivar named 'RutHol5'. Data were collected from a horticulture farm in Watkinsville, Ga. from 6-year-old plants. The average low temperatures ranged from about 15° F. to 30° F. in the winter and about 90° F. to 100° F. in summer.

Botanical classification: *Ilex* 'RutHol5'.

Commercial classification: Ornamental, landscaping.

Parentage: Open pollinated cross between two F1 seedlings from original cross of *Ilex crenata* (unpatented) and *Ilex maximowicziana* (unpatented).

Growth and propagation:

- *Propagation type*.—Vegetative terminal cuttings.
- *Growth rate*.—Moderate.
- *Root description*.—Typically about 5-10 roots arising from the base of the cuttings.
- *Rooting habit*.—Strong.

Plant description:

- *Habit*.—Of 6-year-old plant in field — narrow, upright growth, densely conical with widest spread in middle of the canopy and narrowing at the top; side branches prone to drooping.
- *Usage*.—Various uses, including landscaping, ornamental, container, border, hedge, and mass planting.
- *Vigor*.—Moderate.

Size of 6-year-old plant:

- *A. Height*.—From soil level to top of plant, about 108 inches.
- *B. Width* (*at widest portion*).—About 34 inches.
- *C. Ratio* (*h:w*).—About 3.2.

Branch/stem (terminal tuft):

- *A. Quantity*.—Numerous, with an average of about 26 main branches and about 50-60 lateral branches per main branch.
- *B. Length*.—About 35-70 cm.
- *C. Base diameter*.—About 3-4 mm at about 15 cm from tip.
- *D. Branch angle*.—About 55-65° from center.
- *E: Odor* (*of bruised stem*).—None detected.
- *F. Internode length*.—About 0.5-1.5 cm.
- *G: Color* (*R.H.S.*).—Yellow-Green 146C.
- *H: Strength of lateral branches*.—Moderate to weak.
- *I: Texture/pubescence*.—Sparsely hispid.
- *J: Shape*.—Ridged, 5-sided.

Leaf:

- *A. Leaf type*.—Simple.
- *B. Color* (R.H.S.).—Upper surface — emerging leaves are reddish colored (closest to RHS Purple 77A); mature leaves are closest to Greyed-Green N189A, but are darker in color (more black-green). Lower surface — emerging leaves are Greyed-Orange 177A; mature leaves are Yellow-Green 148A.
- *C. Mature size* (*l×w*).—About 35 mm×about 14 mm, leaf l:w ratio about 2.3-2.5.
- *D. Apex*.—Acute.
- *E. Base*.—Rounded.
- *F. Margin*.—Serrulate.
- *G. Shape*.—Elliptical.
- *H. Lobes*.—Absent.
- *I. Pubescence*.—Smooth, no pubescence.
- *J. Arrangement on stem*.—Alternate.
- *K. Venation*.—Pinnate, coloration (upper and lower) is Yellow green 145A.
- *L. Texture*.—Leathery.
- *M. Odor when crushed*.—None detected.
- *N. Aspect*.—About 55-65°.
- *O. Leaf number*.—Average of about 1.2 per cm/stem.

Petiole:

- *A. Length*.—About 5 mm.
- *B. Shape*.—Reniform.
- *C. Color*.—Yellow-Green N144A.
- *D. Texture/pubescence*.—Moderately hispid.
- *E. Diameter*.—About 1 mm.

Inflorescence:

- *A. Type*.—Solitary or clusters of 1-3.
- *B. Peduncle*.—Length about 4-5 mm.
- *C. Size*.—Height — about 6 mm; diameter — about 15 mm.

Flower:

- *A. Number per inflorescence/stem*.—1 female.
- *B. Axillary or terminal*.—Axillary.
- *C. Symmetry*.—Regular.
- *D. Size* (*l×w*).—About 3 mm by about 4 mm.
- *E. Fragrance*.—None detected.
- *F. Bud*.—Size (L×W) — about 2 mm by about 2 mm; shape — oval; color: Yellow Green 144C; texture/pubescence — smooth, no pubescence.
- *G. Petals*.—Number — 4; size (L×W) — about 2.5 mm×about 2.5 mm; shape — ovate; apex — round; base — truncate; margin — smooth, entire; color at peak bloom — Yellow Green 144C for both upper and lower surface; texture; pubescence — smooth, no pubescence; arrangement — symmetric.
- *H. Pedicels*.—Color — Yellow Green 144A; texture/pubescence — moderate pubescence; length — about 4-5 mm; aspect — erect; strength — strong.

*I. Sepals*.—Number — about 4; size (L×W) — about 1.5 mm×1.5 mm; shape — acuminate; texture/pubescence — no pubescence; color — Yellow Green 144A.

*J. Stamens*.—Number — about 4, about 2 mm long, non-functional; anther — missing; no pollen on female plant.

*K. Pistils*.—a. number — about 4; b. stigma — ovate, Orange-White 159D, smooth texture; c. style — about 1.0×0.5 mm (L×W), White 155D, smooth texture d. ovary — about 2×2 mm (L×W), Yellow Green 144A, smooth texture, position is hypogynous.

Fruit

*A. Type*.—Berry-like drupe.

*B. Immature fruit*.—Size (L×W) — about 4 mm by about 3 mm; smooth texture; no pubescence; color — Yellow Green 144A.

*C. Mature fruit*.—Size (L×W) — about 5 mm by about 4-5 mm; smooth texture; color — Black 202A.

Seed:

*A. Number per fruit*.—About 4.

*B. Size (L×W)*.—About 5 mm by about 3 mm.

*C. Color*.—Greyed Orange 165D.

Weather/temperature tolerance: Not fully determined. Plants of the new *Ilex* have been grown in USDA zone 8a. Parental species have survived down to −5° F. with no damage in Blairsville, Ga.

Disease/pest resistance: To date, plants of the new *Ilex* have been observed to have resistance to spider mites, *Tetranychus urticae*, which are common to other *Ilex* cultivars.

It is claimed:

1. A new and distinct cultivar of the *Ilex* plant named 'RutHol5' as illustrated and described herein.

* * * * *